United States Patent [19]

Muehlenbein

[11] Patent Number: 4,753,307
[45] Date of Patent: Jun. 28, 1988

[54] DEVICE FOR HYDROSTATIC WEIGHING OF HUMANS

[75] Inventor: James A. Muehlenbein, Villa Park, Ill.

[73] Assignee: Novel Products, Inc., Addison, Ill.

[21] Appl. No.: 109,224

[22] Filed: Oct. 16, 1987

[51] Int. Cl.[4] ............... G01G 21/28; G01G 5/02; F16M 13/00; E04G 1/14
[52] U.S. Cl. ................... 177/244; 177/207; 248/676; 248/DIG. 10; 182/142
[58] Field of Search ............... 177/207, 244; 248/647, 248/676, DIG. 10; 182/142

[56] References Cited

U.S. PATENT DOCUMENTS 3,917,200 11/1975 Johnson ..................... 248/647
3,953,029 4/1976 Boyd ..................... 248/DIG. 10

OTHER PUBLICATIONS

Brochure—Country Technology, p. 26.

Primary Examiner—George H. Miller, Jr.
Attorney, Agent, or Firm—Wood, Dalton, Phillips, Mason & Rowe

[57] ABSTRACT

A device for hydrostatic weighing of humans in existing swimming pools having a cradle for supporting a human body under water, a scale suspending the cradle for measuring the percent body fat of a human, a beam suspending the scale over the pool and a support frame for suspending the beam over the water. The frame includes a hollow base leg, a hollow upright post at the end of the base leg, and an upright post at the poolside end of the base leg so that the beam may be adequately supported. The weight of the human in the cradle is counterbalanced by filling the hollow base leg and hollow upright post with water by means of a hose and valve assembly located at the front of the base leg.

5 Claims, 1 Drawing Sheet

U.S. Patent  Jun. 28, 1988  4,753,307
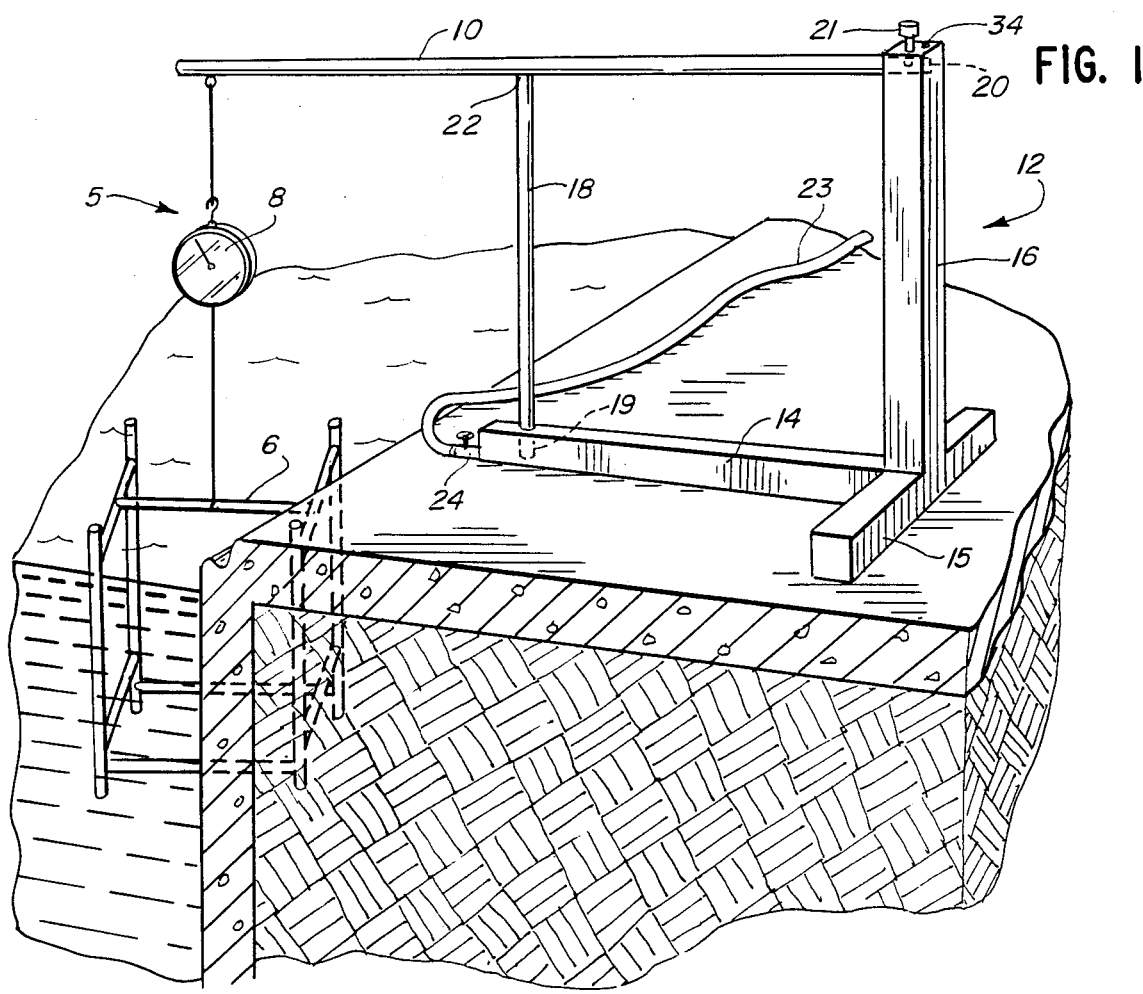
FIG. 1
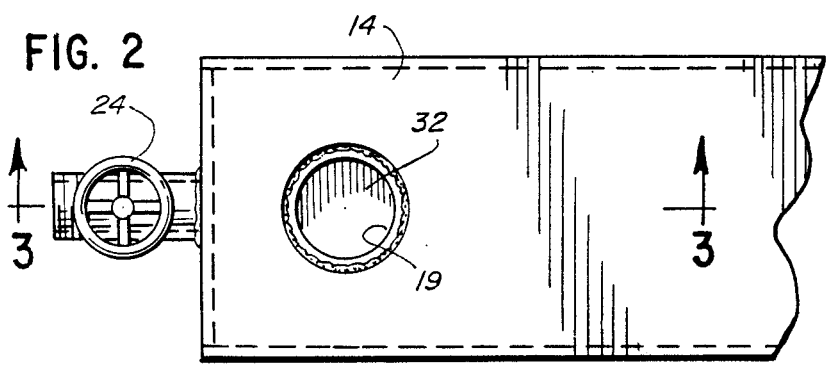
FIG. 2
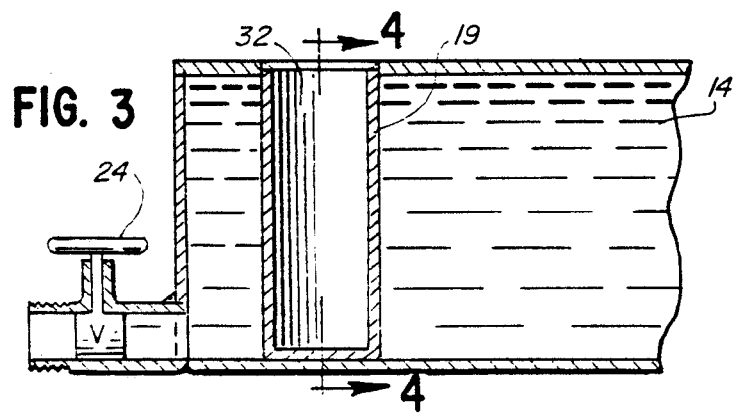
FIG. 3
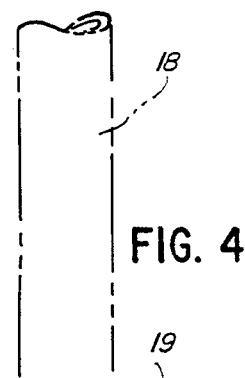
FIG. 4
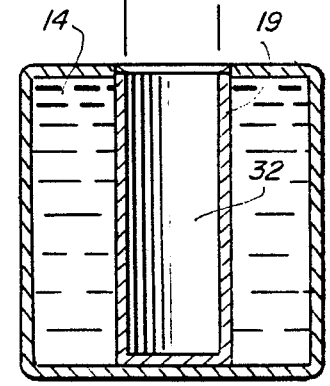

4,753,307

DEVICE FOR HYDROSTATIC WEIGHING OF HUMANS

BACKGROUND OF THE INVENTION

The present invention relates to underwater weighing systems and particularly to portable poolside water weighing systems used in determining the percent of body fat of a human.

The use of permanently fixed hydrostatic underwater weighing systems to determine the percent of body fat of human is known in the prior art. Such systems, however, require their own water tanks, which are both costly and require that large amounts of floor space be permanently dedicated to use in the system.

Primitive portable hydrostatic underwater weighing devices which use existing swimming pools and spas have also been available. Such devices have involved suspending a chair from the diving board, bolting overhead brackets permanently to decks, or putting a chain around rafters and mounting the scale and chair from the chain. These methods are difficult to set up for use, are difficult to use, and do not provide consistently accurate data.

The present invention overcomes one or more of the problems as set forth above.

SUMMARY OF THE INVENTION

In one aspect of the present invention, an underwater weighing devices is provided having a frame supporting a beam which extends horizontally over a swimming pool or the like so that a human, situated in a cradle, may be suspended therefrom and weighed while submersed. The frame supporting the beam has a hollow lightweight base leg, a hollow upright post at the end of the base leg, and a post upright over the poolside end of the base leg. The base leg and upright post located at the end of the base leg are hollow so that they may be filled with water to counterbalance the weight of the suspended and partially submerged human. The water is introduced and drained from the hollow frame through the use of a hose and valve assembly located at the poolside end of the hollow base leg.

It is an object of the present invention to provide for a poolside hydrostatic underwater weighing device which can be used with most pools, positioned next to curved or straight sides of both large or small pools.

It is an additional object of the present invention to provide for a poolside hydrostatic underwater weighing device that is both portable (eliminating the need to permanently dedicate substantial space to its use) and may be easily set up.

Yet another object of the present invention is to provide a weighing device which consistently provides reliable and accurate data for determining body fat.

BRIEF DESCRIPTION OF THE DRAWINGS

FIG. 1 is a perspective view of the hydrostatic underwater weighing device of the present invention;

FIG. 2 is a top view of the poolside end of the base leg;

FIG. 3 is a cross-sectional view taken substantially along line 3—3 of FIG. 2; and FIG. 4 is a cross-sectional view taken substantially along line 4—4 of FIG. 3.

DESCRIPTION OF THE PREFERRED EMBODIMENT

FIG. 1 shows a complete poolside hydrostatic underwater weighing device 5, including a cradle 6 hanging from a scale 8 which in turn is suspended from a beam 10.

The beam 10 is supported by a frame 12 which consists of a hollow lightweight base leg 14, a hollow foot member 15, a hollow column or post 16, and an upright post 18 inserted into a sleeve 19 in the base leg 14. The foot member 15 is welded to the base leg 14 and the upright pole 16 such that the result is a continuous hollow interior between the base leg 14, the foot member 15 and the upright post 16.

The beam 10 is fixed to the column 16 by inserting it into a sleeve 20 and securing it by means of a thumbscrew 21 or the like. Additionally, the beam 10 rests in a semicylindrical recess 22 at the upper end of the upright post 18.

A hose 23 and valve 24 are located at the front of the base leg 14 and communicate with its hollow interior.

Since the hollow base leg 14 and the hollow upright post 16 are to be filled with water before use, it is desirable that the sleeve 19 define a welded well 32 to prevent leakage of water therefrom (see FIGS. 2, 3 and 4). In addition, a hole or vent 34 may be provided at the upper end of the column 16 (so that water leakage therefrom will provide a visual indication that the frame 12 is full during set up.)

In setting up the poolside hydrostatic weighing device 5 for use, the frame 12 is first situated poolside in the orientation shown in FIG. 1. Next, water is introduced into the hollow base leg 14 through the hose 23 and is allowed to flow until the hollow interiors of the base leg 14, the foot member 15 and the upright post 16 are all filled. Once the interiors are filled, the valve 24 may be closed to stop the flow of water.

Simultaneously, the upright post 18 may be inserted into the sleeve 19 and the beam 10 inserted into the sleeve 20 (fastened to the column 16 by the screw 21) and rested on the recess 22 in the upright post 18.

Once the beam 10 is installed, the scale 8 and cradel 6 may be hung so that the cradle is submerged. A person may then be seated in the cradle 6 and, with the person submerged, a weight may be determined from the scale. This weight may then be used to determine the person's body fat.

After use, the beam 10 may be detached from the frame 12 for storage of the device 5 after first removing the cradle 6 and the scale 8. The upright post 18 can then also be removed from the sleeve 19, and the valve 24 may be opened to allow the water in the frame 12 to drain back into the pool. Once the frame 12 has been drained, it can be easily moved and returned to a storage area.

It will be apparent to a skilled artisan that the above described device will be easily moved between storage and use, while at the same time (with the frame 10 filled with water) being stable during use to provide reliable information.

I claim:

1. A portable frame useful for hydrostatic weighing of humans in a pool, comprising:
   a frame for fixedly supporting a beam over the pool, said beam suspending a human from its over-water end for hydrostatic weighing, and said frame including a hollow base leg adjacent the pool at one end, a hollow upright post secured to the end of the base leg remote from the pool with its interior in fluid communication with the interior of said base leg, and means for attaching the beam to the upper end of the hollow post, a second post secured to the poolside end of the base leg and supporting the beam thereon; and means for filling the base leg and hollow post with water.

2. The frame of claim 1, further comprising a drain opening at a low point in said frame for controlled emptying of water from said frame.

3. The frame of claim 2, wherein the drain opening includes a manually operable valve.

4. A portable device for assisting in the hydrostatic weighing of a human in water in an existing swimming pool while the human is suspended in the water for self-controlled total immersion during weighing, comprising:

a hollow frame having a valve for selectively retaining water in and draining water from within the frame, said frame having an elongate hollow base for orientation in a direction extending toward and away from a poolside, an upright column joined to said base member at its end remote from said poolside and having a hollow interior in fluid connection with said base, a foot member extending crosswise of the joined base and column and having a hollow interior in fluid connection with both said column and base;

a beam secured to the upper end of the column and extending outwardly over the base to overhang the pool, a post connected to said base adjacent the pool and having means for cradling said beam above said base end for cantilever over the pool, said frame when placed at poolside filled with water securely supporting a weight on the end of the beam.

5. A device for convenient determination of water-submerged weighing of a human, comprising:

a cradle for supporting a human body under water;

a scale suspending the cradle;

a beam suspending the scale over the water in a swimming pool;

a support frame for the beam including an upright post adjacent the pool, a hollow base extending toward and away from the pool with said post secured to the pool end of the base, and a hollow upright column connected to the hollow base at its lower end, said beam extending generally horizontally over the post and being connected to the column; and means for filling the base and column with water to counterbalance no less than the cradle and scale and a partially submerged human.

* * * * *